United States Patent
Lamouche et al.

(10) Patent No.: US 6,532,821 B2
(45) Date of Patent: Mar. 18, 2003

(54) APPARATUS AND METHOD FOR EVALUATING THE PHYSICAL PROPERTIES OF A SAMPLE USING ULTRASONICS

(75) Inventors: Guy Lamouche, Montreal (CA); Andre Moreau, Saint-Bruno (CA); Martin Lord, Beloeil (CA); Daniel Levesque, Terrebonne (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/901,659

(22) Filed: Jul. 11, 2001

(65) Prior Publication Data

US 2002/0035872 A1 Mar. 28, 2002

Related U.S. Application Data

(60) Provisional application No. 60/217,709, filed on Jul. 11, 2000.

(51) Int. Cl.[7] .................. G01N 29/16; G01N 29/18; G01N 29/20
(52) U.S. Cl. .................. 73/643; 73/602; 73/628; 73/659
(58) Field of Search .................. 73/643, 619, 628, 73/633, 602, 659, 655, 657; 356/432, 446, 450, 336

(56) References Cited

U.S. PATENT DOCUMENTS 4,848,354 A * 7/1989 Angelsen et al. ........... 600/441
5,758,653 A * 6/1998 Schotland ................. 6000/407

(List continued on next page.)

OTHER PUBLICATIONS

Weaver, R.L., "Ultrasonic Diffuse Field Measurements of Grain Size", Non–Destructive Testing and Evaluation in Manufacturing and Construction, 1990, p. 425.

Monchalin, J–P., "Optical Detection of Ultrasound", IEEE Transaction on Ultrasonics, Ferroelectrics Frequency Control, vol. UFFC–33, pp. 485–499, Sep. 1986.

Kuethe A.M. et al., "Foundation of Aerodynamics, Bases of Aerodynamic Design", 4th edition; John Wiley & Sons, New York, 1986; Appendix A: "Dimensional Analysis", p. 44–448.

Guo, C.B. et al., "Scattering of Ultrasonic Waves in Anisotropic Polycrystalline Metals", Acustica, vol. 59, p. 112, 1985.

Willems, H., "A New Method for the Measurement of Ultrasonic Absorption in Polycrystalline Materials", in D.O. Thompson, D.E. Chimenti (Eds.), Review of the Progress in Quantitative Nondestructive Evaluation, vol. 6A, p. 473, 1987.

Scruby, C.B. et al., "Laser–Ultrasonics : Techniques and Applications", Adam Hilger, Bristol, UK, 1990.

*Primary Examiner*—Hezron Williams
*Assistant Examiner*—Jacques Saint-Surin
(74) *Attorney, Agent, or Firm*—Marks & Clerk (57) ABSTRACT

A method is disclosed for evaluating the physical properties of a sample, for example, the grain size in a polycrystalline material. An ultrasound field is generated in a local region of the sample with a non-contact source, such as a pulsed laser, such that the generated ultrasound diffuses away from said local region. After waiting until the generated ultrasound field has reached a diffusion regime, the resulting ultrasound field is measured with a non-contact detector. Parameters are adjusted in a mathematical model describing the predicted behaviour of the ultrasound field in the diffusion regime to fit the detected ultrasound field to the mathematical model. In this way, parameters dependent on the physical properties of the sample, such as the diffusion coefficient and absorption coefficient, can be derived. The grain size, for example, can be estimated from these parameters preferably by calibrating the diffusion coefficient to grain size.

33 Claims, 5 Drawing Sheets

Laser-ultrasonic apparatus.

U.S. PATENT DOCUMENTS

| | | | |
|---|---|---|---|
| 5,804,727 A | * 9/1998 | Lu et al. | 73/597 |
| 5,905,261 A | * 5/1999 | Schotland et al. | 600/476 |
| 5,938,611 A | * 8/1999 | Muzilla et al. | 600/455 |
| 5,964,706 A | * 10/1999 | Mo et al. | 600/443 |
| 6,010,456 A | * 1/2000 | Rhyne | 600/447 |
| 6,041,020 A | * 3/2000 | Caron et al. | 367/149 |
| 6,057,927 A | 5/2000 | Lévesque et al. | 356/432 T |
| 6,092,419 A | * 7/2000 | Dixon et al. | 73/602 |
| 6,095,977 A | * 8/2000 | Hall et al. | 600/443 |
| 6,155,980 A | * 12/2000 | Chiao et al. | 600/447 |
| 6,198,538 B1 | * 3/2001 | Klimek et al. | 356/432 |
| 6,309,356 B1 | * 10/2001 | Ustuner et al. | 600/443 |
| 6,321,601 B1 | * 11/2001 | Maris | 73/657 |
| 6,343,510 B1 | * 2/2002 | Neeson et al. | 73/602 |
| 6,350,240 B1 | * 2/2002 | Song et al. | 600/443 |
| 6,381,019 B1 | * 4/2002 | Maris | 356/432 |

* cited by examiner

Figure 1: Laser-ultrasonic apparatus.

APPARATUS AND METHOD FOR EVALUATING THE PHYSICAL PROPERTIES OF A SAMPLE USING ULTRASONICS

CROSS REFERENCE TO RELATED APPLICATIONS

This application claims priority under 35 USC 119(e) from U.S. provisional application No. 60/217,709, filed Jul. 11, 2000.

BACKGROUND OF THE INVENTION

1. Field of the Invention

The present invention relates to the field of ultrasonics, and more particularly to a method and apparatus for evaluating the physical properties of a sample. The invention can, for example, be used for measuring the diffusion coefficient of ultrasound in a substance, for measuring the absorption coefficient of ultrasound in a substance and for evaluating grain size in a polycrystalline material.

2. Description of Prior Art

Ultrasonic measurement techniques generally involve generating an ultrasonic pulse in an object, and then detecting the signal after propagation in the object to determine its geometrical, microstructural, and physical properties. This technique is advantageous because it is nondestructive and because it can probe the interior of materials. Conventional ultrasonic devices have been developed which involve the use of transducers, including piezoelectric and electromagnetic acoustic transducers (EMATs). Another ultrasonic technique is laser-ultrasonics, wherein one laser with a short pulse is used for generation and another laser coupled to an optical interferometer is used for detection. The detection laser is either a long pulse or continuous laser. Either laser may be coupled to the material under test through an optical fiber for ease of handling.

This approach is advantageous because it does not require either the generation laser or the laser-interferometer detector to be in contact or close to the object. Furthermore, unlike an EMAT or piezoelectric transducer, the generation laser and laser-interferometer are not subject to precise orientation requirements. Details about laser-ultrasonics can be found in C. B. Scruby, L. E. Drain, "Laser-ultrasonics: techniques and applications", Adam Hilger, Bristol, UK 1990 and J.-P. Monchalin, "Optical detection of ultrasound," IEEE Trans. Ultrason. Ferroelectr. Freq. Control, 33, 485 (1986).

The absorption coefficient of ultrasound is one parameter that characterizes the physical properties and the interaction of ultrasound with the microstructure of the material. The variation of the absorption coefficient with temperature and ultrasound frequency can provide information about internal friction, relaxation phenomena, magnetic properties of the material, dislocation density, phase transformations, or specific microstructural structures. The simplest approach to the measurement of the absorption is to observe the free decay in the amplitude of a vibration mode of a sample. Another popular approach is to use a forced vibration where one measures the phase difference between the driving system and the vibration of the sample. Both approaches are limited to samples with specific geometries and each measurement only gives the absorption coefficient at one frequency and one temperature. Performing a full study of absorption as a function of frequency and temperature can be quite time consuming.

Ultrasound absorption can also be estimated from the attenuation of propagating waves. A serious limitation to this approach is the difficulty of separating the attenuation due to absorption mechanisms from that due to other phenomena like diffraction, scattering by grains, or scattering by rough surfaces. In 1987, Willems proposed a reverberation technique in which an ultrasonic pulse is first generated at the surface of a sample, then propagates in the material and, due to the finite size of the sample, fully insonifies the latter with incoherent ultrasound after some time. [H. Willems, "A New Method for the Measurement of Ultrasonic Absorption in Polycrystalline Materials", in D. O. Thompson, D. E. Chimenti (Eds.), Review of the Progress in Quantitative Nondestructive Evaluation, Vol. 6A, p.473, 1987] The measured decrease of the ultrasound amplitude with time can then be solely attributed to absorption mechanisms. When a short laser pulse is used to generate ultrasound, a very wide range of ultrasonic frequencies can be observed. A single measurement then allows the determination of the ultrasound absorption coefficient at many frequencies at once. The main limitation of this technique is that it is restricted to samples with finite volume, making it inappropriate for online measurement.

In 1985, Guo et al. demonstrated experimentally, using conventional transducers and samples of large dimensions, that when an ultrasonic pulse propagates and is scattered by the various structures in a material, it gives rise to an energy cloud of incoherent vibration, termed "diffuse ultrasound", and that this energy cloud spreads as governed by the diffusion equation. [C. B. Guo, D. Holler, and K. Goebbels, "Scattering of Ultrasonic Waves in Anisotropic Polycrystalline Metals", Acustica, vol. 59, p. 112, 1985] The vibration energy not only diffuses but is also absorbed in the material by various mechanisms. By observing the time evolution of the diffuse ultrasound, one can evaluate the diffusion and absorption coefficients of ultrasound. This technique has many advantages over the previous ones. Firstly, it can be applied to large samples. Secondly, it provides the absorption and diffusion coefficients of ultrasound, both parameters being useful for the characterization of the microstructure.

However, because the technique utilizes piezo-electric transducers, it is subject to several limitations. One such limitation is that the piezoelectric transducer must be either in direct contact with the object to be measured, or coupled to that object using some type of bonding material. In addition, delay lines, also called buffer rods, are often used to transport the ultrasound from the object to the transducer. Thus, the ultrasound field to be measured leaks out of the object and into the bond and the transducer where it may be attenuated both by the transducer's, bond's, or delay line's material properties and by the conversion of acoustic energy into electrical energy by the transducer. In practice, this limits the application of the technique to objects which show either a high diffusivity or a high absorption so that the decrease in the sound field energy caused by the sample itself is much larger than the decrease in the sound field energy caused by the transducer and its bond or delay line.

Another limitation of the technique is that the piezoelectric transducer has a relatively narrow bandwidth (or order ±10% to ±50% of the transducer's center frequency). Wideband transduction is usually preferred because a wideband signal can be made narrowband by filtering, whereas a narrowband signal cannot be made wideband.

Yet another limitation of the technique is that the piezoelectric transducer is of relatively large dimensions. Typical dimensions of such transducers may vary from a few mm in diameter to perhaps 25 mm in diameter. Therefore, these transducers cannot spatially resolve the ultrasound field to an accuracy better than about 1 mm in the best cases. This may cause difficulties when measuring the sound field of a small object, or when attempting to measure the spatial dependence of the sound field as a function of position.

In 1990, Weaver proposed an application of the diffusion coefficient of ultrasound to the characterization of the microstructure of materials. [R. L. Weaver, "Ultrasonic Diffuse Field Measurements of Grain Size", Non-Destructive Testing and Evaluation in Manufacturing and Construction, 1990, p. 425] Theoretical considerations show that the diffusion coefficient behaves like the inverse of the ultrasonic attenuation coefficient due to scattering. This coefficient is related to the grain size of polycrystalline materials. Weaver showed experimentally that the diffusion coefficient of ultrasound is affected by thermal treatment for an AISI 1045 steel, which supports the idea that the technique can be used for the non-destructive measurement of grain size. However, he did not specify a method for obtaining precise grain size measurements estimates from the measured diffusion coefficient. Instead, he plots the material's measured diffusivity as a function of frequency and observes that those samples which are expected to have larger grain sizes have higher diffusivity. Therefore, one method of estimating grain size from diffusivity is to build a calibration curve of diffusivity as a function of grain size for a specific material at a specific frequency.

However, the applicants have found that one does not have complete freedom in choosing the frequency, and that different samples may be best measured at different frequencies. For example, if the frequency is too low, too little grain scattering may occur and the sample reaches equipartition of energy only when the ultrasound field has spread so much that its amplitude is too small to be measured accurately. Conversely, if the frequency is too high, the absorption coefficient, which usually increases with frequency, may be so high that the ultrasound energy is largely absorbed before equipartition of energy is attained. Again, this may result in ultrasound amplitudes that are too low to be measured accurately.

Therefore it is an object of the present invention to overcome the afore-mentioned limitations of the prior art.

SUMMARY OF THE INVENTION

According to the present invention there is provided a method of evaluating the physical properties of a sample, comprising generating an ultrasound field in a local region of the sample with a time-varying source of radiation such that the generated ultrasound diffuses away from said local region; waiting until the generated ultrasound field has reached a diffusion regime; detecting the resulting ultrasound field with a non-contact detector; and adjusting parameters in a mathematical model describing the predicted behaviour of the ultrasound field in the diffusion regime to fit the detected ultrasound field to the mathematical model and thereby derive at least one parameter dependent on the physical properties of the sample.

The invention provides a method of measuring the diffuse acoustic field and its time and spatial dependence using a non-contact, preferably wideband, point-like ultrasound detector, and using a preferably wideband, non-contact, ultrasound generator. In a preferred embodiment, advantage is taken of the wideband characteristics of the ultrasound generator and detector by using time-frequency analysis technique to analyze the time and frequency dependence of the measured signal. However, other techniques may be used, such as analog filtering and processing of the data, or a combination of analog and digital processing.

Advantageously, an ultrasound detector with point-like characteristics can be used to take measurements at one or several precisely measured locations on the sample surface.

The mathematical model is typically a diffusion equation with the initial and boundary conditions appropriate to the sample to be measured. The solution to this equation is numerically fitted to the measured ultrasonic signal so as to obtain the ultrasonic diffusion and absorption coefficients of the object being measured.

For a wideband source of ultrasound, such as a pulsed source of radiation, the physical mechanism which transforms the pulsed radiation into ultrasound does not generate all acoustic modes with equal efficiency. However, the diffusion equation accurately describes the ultrasound field only when the ultrasound has locally populated all ultrasonic modes with substantially equal probability. When this arises, the system is said to have attained a local state of equipartition of energy. By "local" it is understood that although the system has not reached a complete state of equilibrium (the ultrasound field is evolving in time), on short time and lengths scales it appears to be in equilibrium. It is in this case that the diffusion equation is valid and the system is said to be in the diffusion regime. Therefore, one must wait some time, typically anywhere from 1 to 100 $\mu$s, for the ultrasound field to attain this state of equipartition. Consequently, the initial conditions to the diffusion-model equation are not those that prevail at the instant of ultrasound generation, but must be taken some time after the instant of ultrasound generation. These initial conditions may rely on an initial-conditions-model describing the ultrasound field some time after the instant of ultrasound generation. Another possibility is to obtain the initial-conditions by measuring the ultrasound field some time after the instant of ultrasound generation. Yet another possibility is to use a combination of a model and measurements. For example, the model may assume one-dimensional behaviour and, because of this assumption, the number of measurements of the ultrasound field required to provide an accurate description of the initial conditions may be greatly reduced. Preferably, all known information or reasonable assumptions regarding the initial conditions are utilized to reduce the number of measurements required.

In 1987, Willems [H. Willems, "A New Method for the Measurement of Ultrasonic Absorption in Polycrystalline Materials", in D. O. Thompson, D. E. Chimenti (Eds.), Review of the Progress in Quantitative Nondestructive Evaluation, Vol. 6A, p.473, 1987] showed how the absorption coefficient measured using the reverberant technique may be used to estimate the amount of plastic strain present in a cold rolled sample. The absorption coefficient measured using the present invention can also do the same.

In another aspect the invention also provides an apparatus for evaluating the physical properties of a sample, comprising a time-varying source of radiation for generating an ultrasound field in a local region of the sample such that the generated ultrasound diffuses away from said local region; a non-contact detector for detecting the resulting ultrasound field with a delay such that the generated ultrasound field has reached a diffusion regime; and an analyzer for adjusting parameters in a mathematical model describing the predicted behaviour of the ultrasound field in the diffusion regime to fit the detected ultrasound field and thereby derive at least one parameter dependent on the physical properties of the sample. This parameter may be used to infer other derived quantities. For example, the absorption coefficient may be used to infer the amount of plastic deformation in a metal or the yield strength of a metal, and the diffusion coefficient may be used to infer the grain size of a polycrystalline aggregate.

Having written a general description of the invention, we now describe specific aspects in more detail.

Preferably, the ultrasound generator is a pulsed source of radiation because this ultrasound generator can be wideband and allows for various source geometries, although narrowband electromagnetic acoustic transducers (EMAT) could be used as well in some special cases. Preferably the pulsed source of radiation is a pulsed laser, although a flash lamp, a pulsed source of x-rays, a pulsed electron gun, a pulsed source of ions, or a pulse of atomic particles, or any other ultrasound-generating source of radiation could be used.

In a preferred embodiment, a non-contact, point-like, ultrasound detector is used to detect the ultrasound.

In the preferred embodiment, the ultrasound detector is a laser interferometer, although any ultrasound detector based on so-called white-light interferometry or on non-interferometric optical (including infrared and UV wavelengths that behave much like optical wavelengths) technique such as knife edge, surface grating, or reflectivity techniques may be used. (Jean-Pierre Monchalin. <<Optical detection of ultrsound>> IEEE Transactions on Ultrasonics, Ferroelectrics, and Frequency Control, Vol. UFFC-33, No. 5, September 1986. p. 485–499.) However, the output of the ultrasound detector should either be linear with ultrasound amplitude (or energy), or could be made linear by the application of a suitable calibration.

Preferably, the interferometer's output signal is wideband so as to measure as much as possible of the full bandwidth of the generated ultrasonic signal. Preferably, the ultrasound detector will sense a point-like location on the surface of the sample. Point-like in this context means that the dimensions of the location that is being sensed are small compared to the shortest acoustic wavelength being measured. This is desirable, but not absolutely necessary, because if the sensing location is larger, the sample motion caused by the ultrasound will be averaged out and sensitivity will be decreased.

Point-like also means that the dimensions of the location that is being sensed are sufficiently small to provide an accurate measurement of the position of that location. Also, although the detection location is usually on the surface of an object, the detection location may also be inside a transparent object. For example, one can imagine a small reflective particle, or a metallic interface being located inside a piece of glass. This small reflective particle or metallic interface would then reflect the laser light that would be used by the laser interferometer to sense the acoustic amplitude at that location.

Preferably, the processor is composed of a digitizer and a computer. The digitizer converts the analog output of interferometer into a digital signal suitable for further analysis and calculations. The computer provides means to store the digital information at least temporarily while the analysis is being performed, and provides a means to apply various algorithms to best extract the diffusion and absorption coefficients, as well as other derived physical quantities. However, the processor may also be analog (as opposed to digital), although these processors provide less flexibility, and sometimes only provide for the approximate implementation of the analysis algorithms. The computer also stores the diffusion equation and calculates the ultrasound diffusion and absorption coefficients.

Preferably, a range of ultrasonic frequencies is selected such that these frequencies are high enough to cause enough scattering so that the equipartition of energy is locally attained before the ultrasound has diffused away from the detection location, and low enough so that the equipartition of energy is locally attained and the diffuse signal reaches the detection location before the ultrasound is absorbed.

Preferably, a numerical time-frequency analysis technique is used to analyze the time and frequency dependence of the measured signal. Preferably, a short time Fourier transform technique with a low leakage window can be used.

The mathematical model employed may be based on the diffusion equation solved with the initial and boundary conditions appropriate to the object to be measured. The solution is numerically fitted to the measured ultrasonic signal so as to obtain the ultrasonic diffusion and absorption coefficients of the object being measured. In this method, the initial conditions are taken as a model distribution of the acoustic field some time after the instant of ultrasound generation, when the ultrasound field has attained a local equipartition of energy. The initial conditions can also be determined by measuring the energy distribution of the ultrasonic field at any time in the diffusive regime.

It is also understood that a material may not have a single diffusion coefficient. For example, an anisotropic material having orthotropic symmetry may have three coefficients, one for each of the three spatial dimensions. This particular example and the more general case can be taken into account in a multi-dimensional diffusion model and initial conditions, and by a suitable set of measurements.

The fitted diffusion coefficient can be related to the grain size of a polycrystalline aggregate. Dimensional analysis states that "If an algebraic equation expresses a relation among physical quantities, it can have meaning only if the terms involved are alike dimensionally". This quote and a formal procedure to apply dimensional analysis can be found in the following reference: Arnold M. Kuethe and Chuen-yen Chow; "Foundation of Aerodynamics, Bases of Aerodynamic Design" $4^{th}$ edition; John Wiley & Sons, New York, 1986; Appendix A: "Dimensional Analysis" p. 444–448. Although such a formal analysis was made, what follows is an informal description which perhaps better captures the idea behind the proposed method.

For the diffusive propagation of ultrasound, one may choose as a basic set of variables with fundamentally different dimensions, the variables: $k=2\pi/\lambda$ where $\lambda$ is the acoustic wavelength, also called the wave number (units of 1/length); c, the sound velocity (units of length/time); and $\rho$, the materials' mass density (units of mass/length$^3$). Other basic sets are also possible, but insofar as these other variables can be constructed from the above variables (for example, k can be replaced by the frequency, f, as long as $k=2\pi f/c$), the argument below can be made without loss of generality.

Given that D, the diffusivity, is expressed in units of length$^2$/time, a dimensionless combination of D with the above basic set of variables is Dk/c. In a polycrystalline aggregate, one may model the propagation of ultrasound as a random walk of phonons that are scattered by the grains. In this case, D=cl/3, where l is the mean scattering length. However, the random walk model is not totally appropriate because each time a phonon is scattered, its propagation direction after scattering remains somewhat correlated with its propagation direction before scattering. Moreover, in a polycrystalline aggregate, scattering of ultrasound occurs when the ultrasound travels from one grain having a specific acoustic impedance to another grain having another acoustic impedance. Thus the mean scattering length should be strongly related to the dimensions of the grains. In particular, if a mean grain size can be defined in a meaningful manner (such as for equiaxed grains), these dimensions may be taken as the mean grain size. Thus, more generally, one expects that D is related with l, which is itself related to the dimensions of the grains or "grain size", d. The dimensionless quantity for grain size is kd. Therefore, one would expect that there should be a general relationship between Dk/c and kd.

Instead of assuming a specific relationship between these two quantities (such as a power law), one may simply plot one variable as a function of the other one and so obtain a "calibration curve". This calibration curve relates the measured diffusivity to grain size, taking into account the wavevector k, and the sound velocity of the material. In other words, as long as all factors affecting D other than k and c are constant, the calibration procedure is reliable. One example of applicability of this calibration curve would be to measure the grain size of a specific metallic alloy where grain size has been affected by thermal processing.

The above analysis is complicated by the fact that there is not one scattering length, but several. The scattering length is different for each ultrasonic mode: longitudinal, transverse, surface waves, plate waves, or other special modes. However, because there is local equipartition of energy, and because the various ultrasonic modes are converted into one-another, D may be considered as a mean diffusion coefficient that is formed by the average of the diffusion coefficients of all acoustic modes, weighted by the probability of occupation for each mode. Therefore, the general conclusion that there must be a general relationship between Dk/c and kd holds.

Consequently, in a further aspect the invention provides a method of determining grain size in a target sample of material, comprising the steps of building a calibration of kd vs Dk/c, based on the measurement of D at one or several values of k on several calibration samples which are similar to the target sample but which differ with respect to their grain size, where D is the diffusion coefficient, k is the wavenumber of the ultrasound, d is the grain size and c is the velocity of sound; measuring the diffusion coefficient D at one or more values of k in the target sample; and determining the grain size in the target sample from the measured diffusion coefficient using said calibration.

BRIEF DESCRIPTION OF THE DRAWINGS

The invention will be described in more details, by way of example only, with reference to the accompanying drawings, in which.

DETAILED DESCRIPTION OF THE PREFERRED EMBODIMENTS OF THE INVENTION

Figure 1:
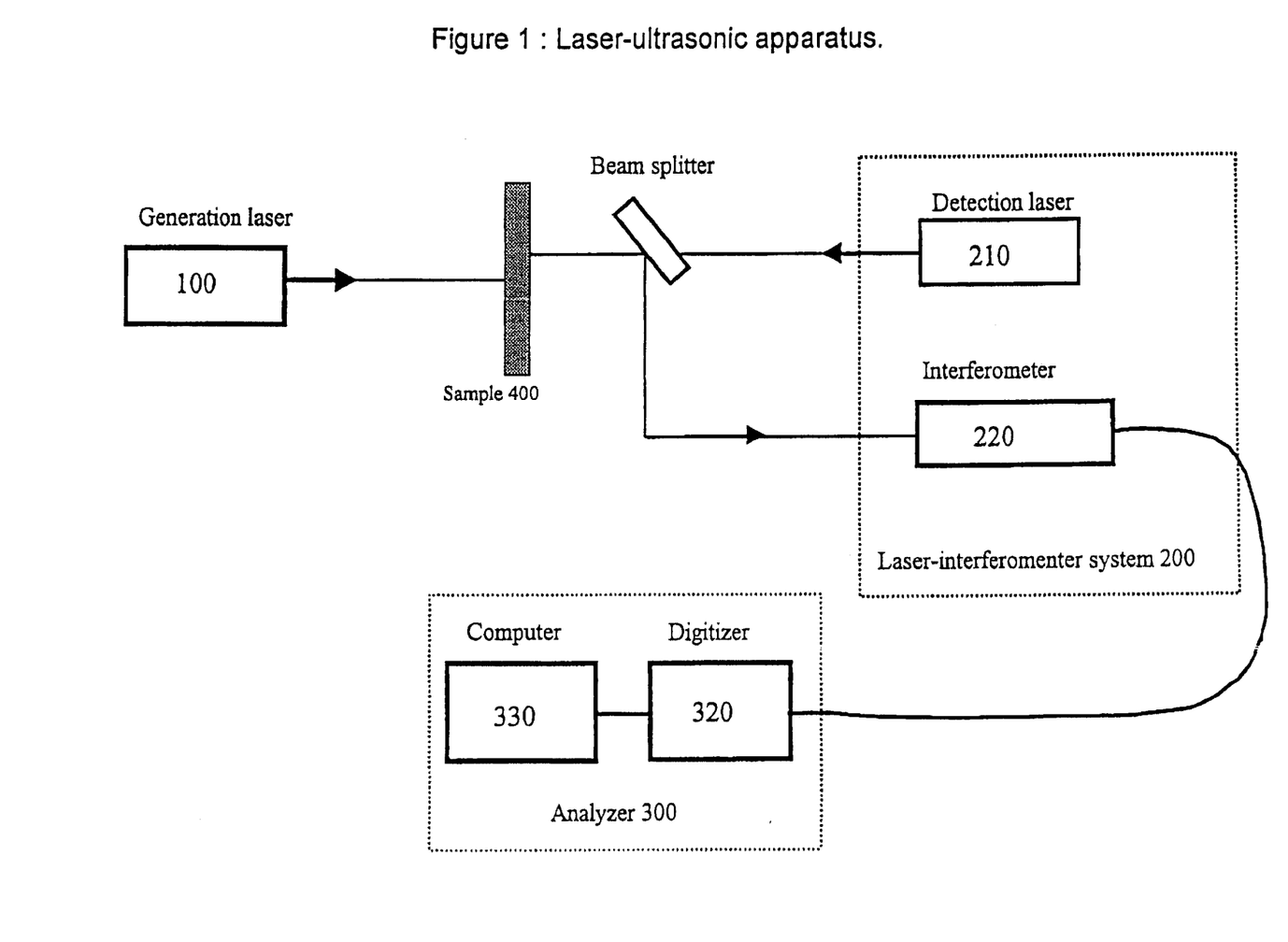
FIG. 1 is a schematic diagram of laser-ultrasonic apparatus.

The preferred embodiment of the proposed laser-ultrasound apparatus is depicted in FIG. 1. The apparatus includes a pulsed generation laser 100, a laser interferometer 200, and an analyzer 300. The sample object 400 under study can be of any geometrical shape. FIG. 1 illustrates the special case where generation and detection are performed on opposite faces of the sample, but they could be performed on the same face.

The apparatus and method operate as follows. The pulse generation laser 100 directs a laser pulse onto the surface of the sample 400. When the laser pulse hits the surface, a broadband ultrasonic pulse is generated in the sample. The originally coherent ultrasonic pulse is scattered by the structures within the material. For example, such structures could be grains in a polycrystalline material. After many scattering events, the ultrasonic field loses most of its spatial coherence and the resulting wave field is termed diffuse. The diffuse field is still somewhat localized near the generation region. The system is now in the diffusion regime and the ultrasonic spectral energy density evolves as governed by a diffusion equation. This diffusion model has been confirmed experimentally and supported by theoretical work. Concurrently, the ultrasonic energy is absorbed through various mechanisms involving dislocation and magnetoelastic effects.

The evolution of the ultrasonic diffuse field is monitored by sensing the surface motion of the sample with the laser-interferometer system 200. From the observed diffuse field evolution, the analyzer evaluates the ultrasonic diffusion and absorption coefficients. In the case of a polycrystalline material, the grain size is also estimated from the value of the diffusion coefficient.

The generation laser 100 emits and directs a laser light pulse onto the surface of the sample 400. Depending on the application, this laser may be a $CO_2$ laser, a Nd:Yag laser, an excimer laser, or any other pulse laser. The generation laser 100 can also be a continuous or long-pulse laser followed by an optical switching device.

The surface displacements caused by the elastic waves are detected by the laser interferometer 200, which outputs a signal representative of the amplitude of surface displacements as a function of time. The laser interferometer may be sensitive to either the normal or in-plane surface displacement, or to both.

The main components of the laser interferometer 200 are (a) a detection laser 210, and (b) an interferometer 220. The interferometer may be a Fabry-Pérot, Michelson, Mach-Zender, photorefractive, photo-emf, or any other type of interferometer with a detection bandwidth that includes the frequency range of interest. An optical fiber system may be installed between the laser-interferometer system 200 and the sample 400, so the former can be located at a distance from the latter.

The time signal output by the interferometer 220 is received at an input 310 by the analyzer 300. The analyzer 300 includes (a) a digitizer or digital sampling device 320, which receives and digitizes the time signal input from the interferometer 220 via input 310, and (b) a personal computer 330 for processing the data.

The personal computer 330 first performs a time-frequency analysis on the time signal provided by the digitizer 320. This gives a spectrogram showing the time evolution of the Fourier components of the output signal. From this time evolution, the personal computer 330 evaluates the absorption and diffusion coefficients of ultrasound at the desired frequencies. In the case of a polycrystalline material, the personal computer 330 can also estimate the grain size from the diffusion coefficient.

The following method is used to evaluate the diffusion coefficient and the absorption coefficient. An ultrasonic pulse is generated in the material from a laser pulse impinging on its surface. The initial ultrasonic energy distribution that appears after many scattering events following the ultrasound generation can be modeled. Based on the generation configuration, this initial distribution may be evaluated totally from theoretical grounds or it may be measured. The initial conditions can also be evaluated partly from theoretical grounds, leaving adjustable parameters that may be fitted from the measurements. In the following, for a quantity $A(\vec{r},t)$ that varies with time and position, we use $A(\vec{r},t,\omega)$ to denote the amplitude of its spectral component evaluated for an angular frequency $\omega$, at a time t, over a time window $\Delta t$, and at a position $\vec{r}$, disregarding the phase factor. The initial distribution of the energy density evaluated at time $t_0$ is thus given by $U(\vec{r},t_0,\omega)$. The spectral energy density evolves in the material according to a diffusion equation including absorption:

$$\frac{\partial U(\vec{r},t,\omega)}{\partial t} = D(\omega)\nabla^2 U(\vec{r},t,\omega) - 2\alpha(\omega)U(\vec{r},t,\omega), \quad (1)$$

where $D(\omega)$ and $\alpha(\omega)$ are respectively the diffusion coefficient and the absorption coefficient for the spectral component of frequency $\omega$.

From the initial distribution at time to and the boundary conditions imposed by the geometry of the sample, one can obtain the spectral energy density, $U(\vec{r},t,\omega)$, from either (a) an analytical expression with adjustable parameters or (b) a numerical procedure allowing to solve the diffusion equation numerically for a given set of adjustable parameters. The parameters to be determined may include either one or both of the diffusion coefficient $D(\omega)$ and the absorption coefficient $\alpha(\omega)$. Preferably, the experimental measurement provides the surface displacement $u(\vec{r},t)$. The spectral component $u(\vec{r},t,\omega)$ is proportional to the square root of the spectral energy density $U(\vec{r},t,\omega)$. The true diffuse field evolution is observed by measuring the surface displacement $u_{exp}(\vec{r},t)$ of the sample with a laser-interferometer system and by digitizing the output of the interferometer.

A time-frequency analysis of the digitized signal is then performed. For a given frequency $\omega$, the resulting spectral component $u_{exp}(\vec{r},t,\omega)$ is fitted with the model function $u(\vec{r},t,\omega)$ by adjusting the unknown parameters, including $D(\omega)$ and $\alpha(\omega)$. The diffusion and absorption coefficients are then evaluated. If the initial energy density distribution is dependent upon one or more adjustable parameters, these parameters are also evaluated during the fitting procedure. Additionally, other adjustable parameters, like the experimental noise level, might be needed in some specific cases. The fitting procedure also allows the estimation of these parameters.

In a preferred embodiment, the analysis may proceed as follows. At each location where measurements of the ultrasound surface amplitude were made, a time-frequency analysis is made using short time Fourier transforms and a low-leakage window (such as the Blackman-Harris window). For all frequencies where the signal to noise ratio was sufficiently large to permit reliable measurements of signal energy density (which is proportional to the squared amplitude) as a function of time, a representation of the energy density versus time is constructed. This representation is then fitted to the model equations to which a constant term is usually added to take into account experimental noise. This fitting procedure may either be done for each measurement location individually, or it may be done for several measurement locations, depending on the model utilized.

Determination of Grain Size

Theoretical considerations suggest that, for bulk measurements (that is for samples where surface waves or other special waves have negligible effects as compared to bulk waves), the diffusion coefficient $D(\omega)$ is proportional to a combination of the inverse of longitudinal $[\alpha_{S,L}(\omega)]$ and transverse $[\alpha_{S,T}(\omega)]$ attenuation coefficients due to the scattering of propagating ultrasonic waves:

$$D = f_T c_T / 6\alpha_{S,T}(\omega) + f_L c_L / 6\alpha_{S,L}(\omega) \quad (2)$$

where $f_T$ and $f_T = 1 - f_L$ are the mixing weights for the transverse and longitudinal contributions to the diffusivity, and where $c_T$ and $C_L$ are the transverse and longitudinal wave velocities, respectively. It is well known that the attenuation coefficient due to scattering is related to the grain size d, taking the simple form of a power law $\alpha_s$ $d^n$ in the various regimes, with n ranging from -1 for geometrical optics limit to 3 in the Rayleigh regime. One can thus conclude that the diffusion coefficient $D(\omega)$ varies with the grain size and that in a simple regime, this variation should take the form of a power law:

$$D(\omega) = A d_{-n}, \quad (3)$$

where the parameters A and n depend upon the nature of the material. Once the parameters A and n are determined from a calibration procedure, the analyzer 300 can give an estimation of the grain size from the measured value of the diffusion coefficient.

More generally, the grain size of a specific sample may be obtained by first building a (graphical or algebraic or numerical) calibration of kd vs Dk/c based on the measurement of D at one or several values of k on several samples which are similar to the sample to be measured, but which differ with respect to the grain size d. In a second step, one measures D at one or several values of k for the sample whose grain size is to be estimated. The grain size d is then obtained using the calibration at the measured value of Dk/c.

The Evaluation of the Absorption Coefficient Alone

Although the method described above is quite general, it is instructive to described a few preferred embodiment for some special cases. In an embodiments where the generation and detection pulses are aligned, whether on the same face or on opposite faces, two limiting cases lead to the simple evaluation of the absorption coefficient alone.

Firstly, if the material is characterized by a small diffusion coefficient or if the initial energy distribution is nearly constant around the detection point, the energy cloud shows almost no diffusion and the decay can be solely attributed to absorption. In that case, the solution to Eq. (1) leads to the following evolution for the spectral component of the surface displacement:

$$u(\vec{r},t,\omega) = C_1 \exp[-\alpha(\omega)t]. \quad (4)$$

where $C_1$, is a constant. Thus, by fitting the measured surface displacement with Eq. (4), one can evaluate the absorption coefficient.

Secondly, if the material is characterized by a large diffusion coefficient or if the initial energy cloud shows a strong gradient near the detection point, like for a very localized initial energy cloud for example, the diffusion occurs very rapidly. In that case, the solution to Eq. (1) leads to:

$$u(\vec{r},t,\omega)=C_1 \exp[-\alpha(\omega)t]/t^{m/4}, \quad (5)$$

where $C_1$ is a constant and m correspond to the dimensionality of the sample. For example, m=1 for a thin rod, m=2 for a thin sheet, and m=3 for a bulk sample. Again, by fitting the measured surface displacement squared-amplitude to Eq. (5), one can evaluate the absorption coefficient.

In order to obtain any of the two cases above, the initial energy distribution can be controlled with the spot size of the generation pulse. The evaluation of the diffusion coefficient alone In an embodiment where the absorption coefficient is very small, and for a very localized initial energy distribution, the solution to Eq. (1) leads to $$u(\vec{r}, t, \omega) = C_1 \left( \frac{\exp\{-r^2 / [4D(\omega)(t - t_{0\mathit{eff}})]\}}{(t - t_{0\mathit{eff}})} \right)^{m/4} \quad (5a)$$

where $C_1$ is a constant and m correspond to the dimensionality of the sample. For example, m=1 for a thin rod, m=2 for a thin sheet, and m=3 for a bulk sample. By fitting the measured surface-displacement squared-amplitude to equation (5a), one can evaluate the diffusion coefficient.

Example 1: Simultaneous measurement of the absorption and diffusion coefficients for a set of three measurement locations and intial conditions where the energy density follows a Gaussian distribution, and application to grain size measurement in steel.

As a first illustration of the use of the invention, it was applied to the evaluation of the absorption and diffusion coefficients of six steel sheets of grade LC. Equation (3) relating the grain size and the diffusion coefficient is also verified.

Figure 2:
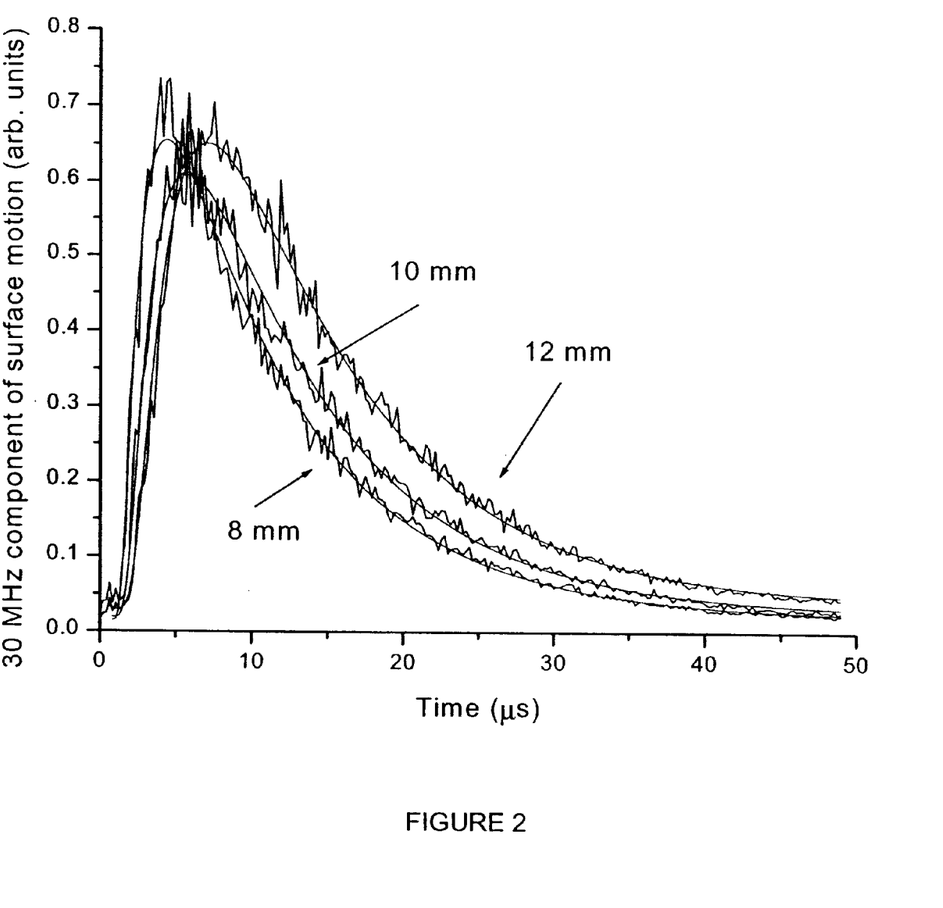
FIG. 2 shows the time evolution of the amplitude of the 30 MHz component of the surface motion at 8 mm, 10 mm and 12 mm from the generation point. Irregular lines are experimental measurements while smooth lines are fitted curves.

The ultrasonic pulse is generated by vaporizing a thin layer of oil on the surface of the sheet with a focused excimer laser pulse. After some scattering events, the ultrasonic pulse gives rise to a spectral energy distribution that is modeled by the following function:

$$U(\vec{r},t_0,\omega) \exp[-r^2/(2\sigma^2)], \quad (6)$$

where the distribution width $\sigma$ and the initial time $t_0$ are adjustable parameters. Due to the geometry of the sample, the sheet is modeled as a two-dimensional infinite plane and the variable $\vec{r}$ represents the measurement location as measured from from the generation point, and r is the modulus of $\vec{r}$. Solving Eq. (1) with the appropriate boundary conditions, one obtains for the surface displacement:

$$u(\vec{r}, t, \omega) = C_1 \exp[-\alpha(\omega)t]\left( \frac{\exp\{-r^2 / [4D(\omega)(t - t_{0\mathit{eff}})]\}}{(t - t_{0\mathit{eff}})} \right)^{1/2} + C_3, \quad (7)$$

where $\alpha(\omega)$ is the absorption coefficient, $D(\omega)$ is the diffusion coefficient, and $C_3$ is the experimental noise level. The parameter $t_{0\mathit{eff}} = t_0 - \sigma^2/(2D(\omega))$ combines the information about the initial time of diffusion and the initial width of the energy distribution in a single adjustable parameter. The evolution of the ultrasonic diffuse field is measured on the opposite face of the sample with a laser-interferometer comprising a long-pulse (pulse duration typically of 10 μs to 1 ms) laser that is frequency modulated by the surface movement, and a Fabry-Pérot interferometer. The output of the interferometer is digitized by a digital oscilloscope and a computer performs a time-frequency analysis of this digitized signal. Typical evolutions are presented in FIG. 2 for the 30 MHz spectral component of the surface movement measured at 8 mm, 10 mm and 12 mm from the generation point. For a given sample, the computer performs simultaneous fits of the observed evolutions at 8 mm, 10 mm, and 12 mm with of Eq. (4) by adjusting the parameters $C_1$, $C_3$, $t_{0\mathit{eff}}$, $\alpha(\omega)$, and $D(\omega)$, using the same values of $t_{0\mathit{eff}}$, $\alpha(\omega)$, and $D(\omega)$ for all fits. Typical fits are also presented in FIG. 2. From those fits, we evaluate the absorption and diffusion coefficients. Values are presented in Table 1 for the six samples studied.

Figure 3:
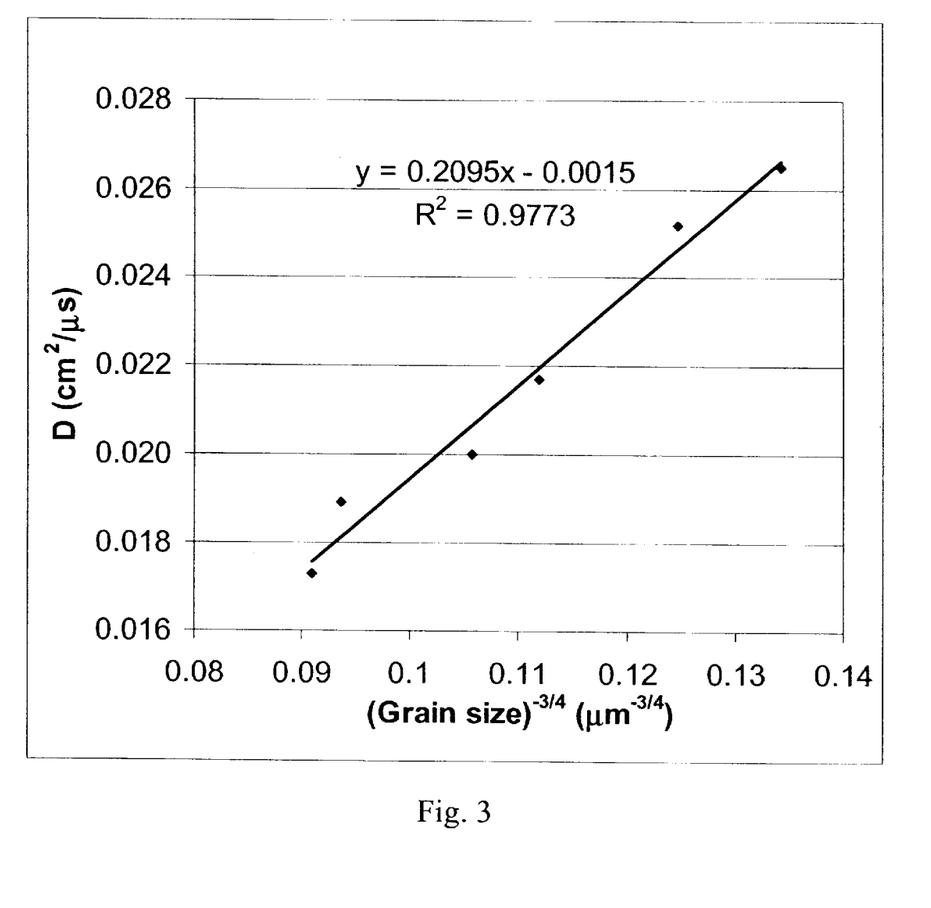
FIG. 3 shows the ultrasonic diffusion coefficient measured at 30 MHz as a function of metallographic grain size for low-carbon steel sheets.

Metallographic measurements of grain sizes were performed on those samples. The measured values are also given in Table 1. FIG. 3 shows that the relation between the diffusion coefficient and the grain size is indeed of the form suggested by Eq. (3) with the exponent n taking the value ¾. From such a calibration curve, further measurement of the diffusion coefficient on another sample allows the evaluation of the grain size.

TABLE 1

Absorption and diffusion coefficients measured with the apparatus and method for six samples of LC grade steel sheets. Grain sizes measured by metallography.

| Sample | Absorption coefficient (dB/μs) | Diffusion coefficient (cm²/μs) | Grain size (μm) |
|---|---|---|---|
| #1 | 0.67 | 0.0173 | 24.5 |
| #2 | 0.64 | 0.0189 | 23.5 |
| #3 | 0.67 | 0.0217 | 18.6 |
| #4 | 0.78 | 0.0265 | 14.6 |
| #5 | 0.65 | 0.0200 | 20 |
| #6 | 0.76 | 0.0252 | 16.1 |

Example 2: Measurement on the absorption coefficient alone with a single measurement and for initial conditions that can be approximated by a nearly constant energy distribution, and application to the measurement of yield strength in steel.

As a second illustration of the use of our invention, we apply it to cases where only the absorption coefficient is evaluated. We first show that the absorption coefficient is sensitive to the density of dislocation. We then demonstrate how the absorption coefficient can be used to estimate the yield strength of steel.

Figure 4:
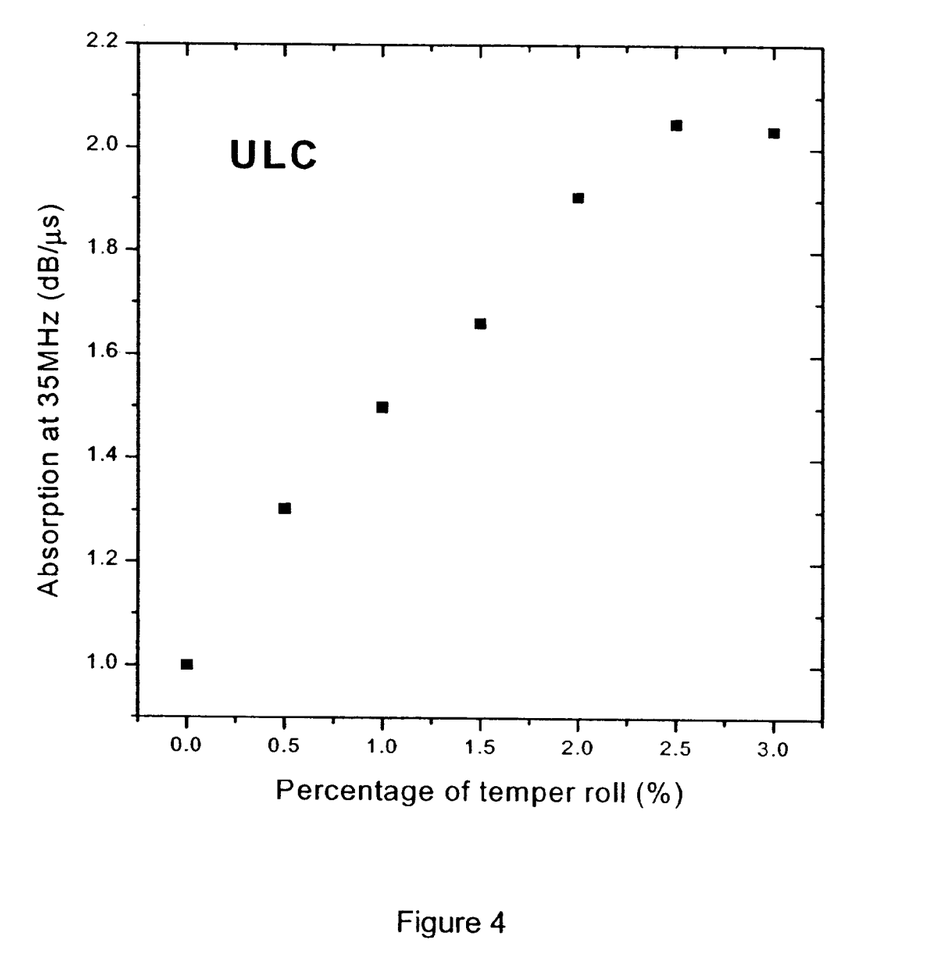
FIG. 4 shows the absorption coefficient measured at 35 MHz as a function of the degree of temper reduction for ultra-low-carbon steel sheets.

Interaction with dislocations is one of the main components of ultrasound absorption in the MHz range. Absorption coefficients were measured with our apparatus on seven thin steel sheets (30 cm×30 cm×1 mm) of grade ultra-low carbon. The samples were exposed to the exact same thermo-mechanical treatment except for various degrees of temper reduction (also called skin-pass). The degree of temper roll influences the density of dislocations. Absorption measurements were performed with the generation and detection aligned, but from opposite faces in a configuration corresponding to a rapidly diffusing energy cloud. To fit the experimental data, Eq. (5) was thus used with m=2 since a thin sheet is a two-dimensional structure. FIG. 4 shows the measured absorption coefficient at 35 MHz as a function of the degree of temper roll. Since the degree of temper roll influences the density of dislocations, FIG. 4 shows that the absorption coefficient of ultrasound is very sensitive to the density of dislocations.

Figure 5:
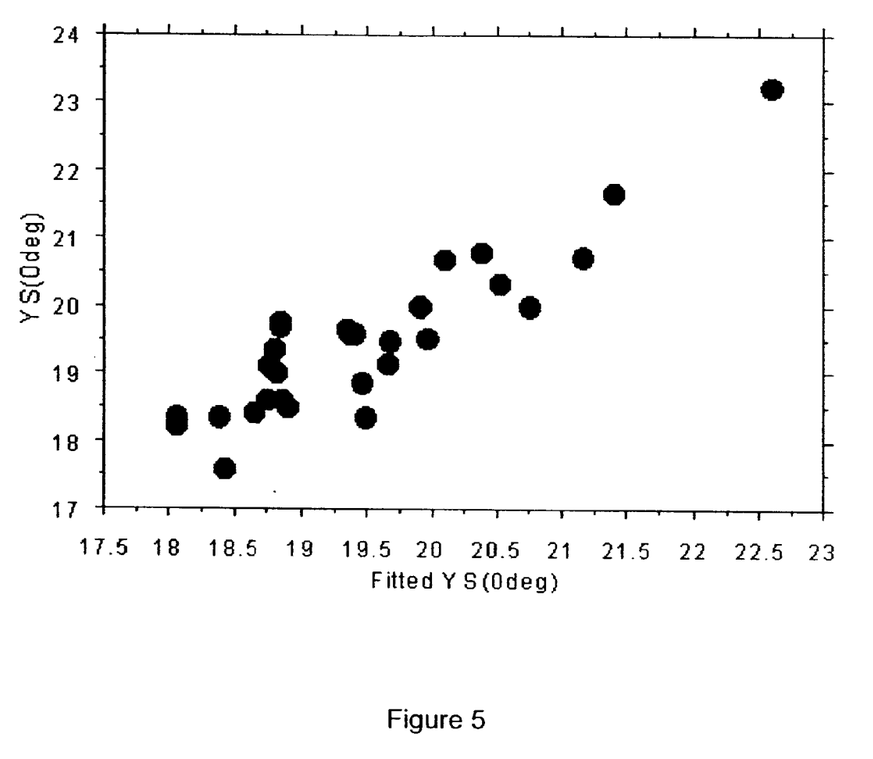
FIG. 5 shows the measured yield strength as a function of the fitted yield strength obtained from a multiple correlation involving the grain size, the texture coefficient $W_{400}$, and the ultrasound absorption as a measure of the dislocation density. In this example, the grain size and texture coefficient were obtained using other ultrasonic measurement methods which are not the subject of this invention.

From the Hall-Petch equation, (E. O. Hall, Proc. Phys. Soc., 1951, Vol. 64B, p. 747; and N. J. Petch, Proc. Swampscott Conf., 1959, M. I. T. Press, p. 54) it is well known that the yield strength of a metal is dependent upon factors like grain size, dislocation density, texture, and chemical composition. As shown above, the ultrasound absorption is sensitive to the density of dislocations and can thus be used to estimate the yield strength. For 29 thin steel sheets (30 cm×30 cm×1 mm) of grade ultra-low carbon, we measured the absorption coefficient with the generation and detection aligned, in a configuration showing very low diffusion. Equation (4) was thus used to evaluate the absorption coefficient. FIG. 5 shows the measured yield strength as a function of the fitted yield strength, the latter resulting from a multiple correlation involving the grain size, the texture coefficient $W_{400}$, and the absorption coefficient as a measure of the dislocation density. The grain size was evaluated from ultrasound attenuation and the texture coefficient was evaluated using ultrasound spectroscopy (D. Levesque et al. "Laser-ultrasound spectroscopy appratus and method with detection of shear resonances for measuring anisotropy, thickness, and other properties" U.S. Pat. No. 6 057 927). The good relationship obtained in FIG. 5 shows that ultrasound absorption is an important parameter for the characterization of materials.

The described invention therefore provides an improved ultrasound measurement apparatus and method for the non-contact, wideband measurement of the diffuse ultrasonic field and to obtain the diffusion and absorption coefficients describing this diffuse ultrasound field. There is also a need for an improved method to relate the measured diffusion coefficient to the grain size of polycrystalline aggregates.

We claim:

1. A method of evaluating the physical properties of a sample, comprising:
   generating an ultrasound field in a local region of the sample with non-contact source such that the generated ultrasound diffuses away from said local region;
   waiting until the generated ultrasound field has reached a diffusion regime wherein the ultrasound field has locally populated all ultrasonic modes with substantially equal probability;
   monitoring the evolution of the resulting ultrasound field with a non-contact detector while said ultrasound field is in the diffusion regime; and
   adjusting parameters in a mathematical model describing the predicted behavior of the ultrasound field in the diffusion regime to fit the detected behavior of the ultrasound field to the mathematical model and thereby derive at least one parameter dependent on the physical properties of the sample.

2. A method as claimed in claim 1, wherein said at least one parameter is an absorption coefficient for the sample.

3. A method as claimed in claim 1, wherein said at least one parameter is a diffusion coefficient for the sample.

4. A method as claimed in claim 3, further comprising the step of estimating the grain size of materials from said diffusion coefficient.

5. A method as claimed in claim 4, wherein said grain size is obtained from said diffusion coefficient by building a calibration of kd vs Dk/c based on the measurement of D at one or several values of k on several samples which are similar to the sample to be measured, but which differ with respect to their grain size, where D is the diffusion coefficient, k is the wavenumber of the ultrasound, d is the grain size, and c is the velocity of sound.

6. A method as claimed in claim 1, wherein said diffuse ultrasound field is generated with a time-varying source of radiation.

7. A method as claimed in claim 6, wherein said non-contact source is a laser.

8. A method as claimed in claim 7, wherein said laser is a pulsed laser.

9. A method as claimed in claim 1, wherein said non-contact detector is a laser interferometer.

10. A method as claimed in claim 1, wherein said mathematical model is a diffusion equation for the ultrasound field.

11. A method as claimed in claim 10, wherein the diffusion equation is:

$$\frac{\partial U(\vec{r}, t, \omega)}{\partial t} = D(\omega)\nabla^2 U(\vec{r}, t, \omega) - 2\alpha(\omega)U(\vec{r}, t, \omega),$$

wherein $U(\vec{r}, t_0, \omega)$ represents the spectral energy density in the sample at time t and $D(\omega)$ and $\alpha(\omega)$ are respectively the diffusion coefficient and the absorption coefficient for the spectral component of frequency $\omega$.

12. A method as claimed in claim 11, wherein a time-frequency analysis is performed on the detected ultrasound field to fit it to the mathematical model.

13. A method as claimed in claim 1, wherein the ultrasound field contains a range of frequencies in which there is sufficient scattering to permit a local equipartition of energy before the ultrasound energy is completely carried away or completely absorbed.

14. A method as claimed in claim 1, wherein the ultrasound detector is wideband.

15. A method as claimed in claim 1, wherein the ultrasound detector senses a point-like location on the sample.

16. A method as claimed in claim 1, wherein said sample contains a polycrystalline aggregate and the grain size of said aggregate is determined from said derived at least one parameter.

17. A method of determining grain size in a target sample of material, comprising the steps of:
   building a calibration of kd vs Dk/c, based on the measurement of D at one or several values of k on several calibration samples which are similar to the target sample but which differ with respect to their grain size, where D is the diffusion coefficient, k is the wavenumber of the ultrasound, d is the grain size and c is the velocity of sound;
   measuring the diffusion coefficient D at one or more values of k in the target sample; and
   determining the grain size in the target sample from the measured diffusion coefficient using said calibration.

18. A method of evaluating the physical properties of a sample, comprising:
   generating an ultrasound field in a local region of the sample with a pulsed laser such that the generated ultrasound diffuses away from said local region;
   waiting until the generated ultrasound field has reached a diffusion regime wherein the ultrasound has locally populated all ultrasonic modes with substantially equal probability;
   monitoring the evolution of the resulting ultrasound field with a non-contact, point-like detector; and adjusting parameters in a diffusion equation describing the predicted behavior of the ultrasound field in the diffusion regime to fit the detected behavior of the ultrasound field to the diffusion equation and thereby derive at least one sample parameter selected from the group consisting of the absorption coefficient and the diffusion coefficient.

19. A method as claimed in claim 18, wherein said ultrasound field is monitored with a laser interferometer.

20. An apparatus for evaluating the physical properties of a sample, comprising:
a time-varying source of radiation for generating an ultrasound field in a local region of the sample such that the generated ultrasound diffuses away from said local region;
a non-contact detector for monitoring the evolution of the resulting ultrasound field while in a diffusion regime wherein the ultrasound has locally populated all ultrasonic modes with substantially equal probability; and
an analyzer for analyzing the portion of said resulting ultrasound field that is in a diffusion regime and adjusting parameters in a mathematical model describing the predicted behavior of the ultrasound field in said diffusion regime to fit the detected behavior of the ultrasound field and thereby derive at least one parameter dependent on the physical properties of the sample.

21. An apparatus as claimed in claim 20, wherein said non-contact detector is a point-like detector.

22. An apparatus as claimed in claim 21, wherein said non-contact detector is a laser interferometer.

23. An apparatus as claimed in claim 20, wherein said time-varying source of radiation is a pulsed laser.

24. An apparatus as claimed in claim 20, wherein said analyzer is programmed to perform a time-frequency analysis on the detected ultrasound field to fit it to the mathematical model.

25. An apparatus as claimed in claim 24, wherein said analyzer comprises a computer and a digitizer.

26. An apparatus as claimed in claim 25, wherein said mathematical model describing the predicted behavior of the ultrasound field in the diffusion regime is stored in said computer.

27. An apparatus as claimed in claim 26, wherein said mathematical model is a solution to the diffusion equation for the ultrasound field.

28. An apparatus as claimed in claim 27, wherein the diffusion equation whose said solution is stored in said computer is:

$$\frac{\partial U(\vec{r}, t, \omega)}{\partial t} = D(\omega)\nabla^2 U(\vec{r}, t, \omega) - 2\alpha(\omega)U(\vec{r}, t, \omega),$$

wherein $U(\vec{r}, t_0, \omega)$ represents the spectral energy density in the sample at time t and $D(\omega)$ and $\alpha(\omega)$ are respectively the diffusion coefficient and the absorption coefficient for the spectral component of frequency $\omega$.

29. An apparatus claimed in claim 25, wherein said computer is programmed to estimate the grain size of materials from said diffusion coefficient.

30. An apparatus as claimed in claim 29, wherein said computer is programmed to obtain said grain size from said diffusion coefficient by building a calibration of kd vs Dk/c based on the measurement of D at one or several values of k on several samples which are similar to the sample to be measured, but which differ with respect to their grain size, where D is the diffusion coefficient, k is the wavenumber of the ultrasound, d is the grain size, and c is the velocity of sound.

31. An apparatus for determining grain size in a target sample of material, comprising:
a computer programmed to store a calibration of kd vs Dk/c, based on the measurement of D at one or several values of k on several calibration samples which are similar to the target sample but which differ with respect to their grain size, where D is the diffusion coefficient, k is the wavenumber of the ultrasound, d is the grain size and c is the velocity of sound; and
an ultrasonic measuring system for measuring the diffusion coefficient D at one or more values of k in the target sample; and
said computer being programmed to determine the grain size in the target sample from the measured diffusion coefficient using said calibration.

32. An apparatus for evaluating the physical properties of a sample, comprising:
a pulsed laser for generating an ultrasound field in a local region of the sample such that the generated ultrasound diffuses away from said local region;
a non-contact, point-like ultrasound detector for monitoring the evolution of the resulting ultrasound field with a with a delay such that the generated ultrasound field has reached a diffusion regime wherein the ultrasound has locally populated all ultrasonic modes with substantially equal probability; and
an analyzer for adjusting parameters in a diffusion equation describing the predicted behavior of the ultrasound field in the diffusion regime to fit the detected behavior of the ultrasound field and thereby derive at least one sample parameter selected from the group consisting of the absorption coefficient and the diffusion coefficient.

33. An apparatus as claimed in claim 32, wherein said ultrasound detector is a laser interferometer.

* * * * *

UNITED STATES PATENT AND TRADEMARK OFFICE
CERTIFICATE OF CORRECTION

PATENT NO.     : 6,532,821 B2                                                            Page 1 of 1
DATED          : March 18, 2003
INVENTOR(S)    : Guy LaMouche It is certified that error appears in the above-identified patent and that said Letters Patent is hereby corrected as shown below:

Column 1,
Line 10, insert:
-- Statement regarding federally sponsored research or development
"The government of the United States of America has rights in this invention pursuant to Cooperative Agreement No. DE-FC07-93ID13205 awarded by the U.S. Department of Energy" --

Signed and Sealed this

Twenty-sixth Day of August, 2003

JAMES E. ROGAN
*Director of the United States Patent and Trademark Office*